US00H002082H

(19) United States

(12) Statutory Invention Registration (10) Reg. No.: US H2082 H

Johannes et al. (43) Published: Sep. 2, 2003

(54) OXIDIZED NORMAL PARAFFINIC PRODUCTS AND THEIR APPLICATION

(75) Inventors: Derick Raymond Johannes, Sasolburg (ZA); Johannes Jurie Human, Sasolburg (ZA)

(73) Assignee: Schumann Sasol (SA), Johannesburg (ZA)

(21) Appl. No.: 09/770,378

(22) Filed: Jan. 29, 2001

(65) Prior Publication Data

US 2002/0039974 A1 Apr. 4, 2002

Related U.S. Application Data

(60) Provisional application No. 60/178,325, filed on Jan. 27, 2000.

(51) Int. Cl.[7] ..... C09K 7/00

(52) U.S. Cl. ..... 508/575; 507/267; 518/728; 423/26

*Primary Examiner*—Michael J. Carone

*Assistant Examiner*—Aileen B. Felton

(74) *Attorney, Agent, or Firm*—Young & Thompson

(57) ABSTRACT

A flotation agent including an oxidized paraffinic product which may be a Fischer-Tropach reaction product obtained by way of the Fischer-Tropsch reaction from carbon monoxide and hydrogen feed. A process for the production of a synthetic fatty acid suitable as a substitute for naturally derived fatty acid in various applications is also disclosed.

7 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OXIDIZED NORMAL PARAFFINIC PRODUCTS AND THEIR APPLICATION

FIELD OF THE INVENTION

This invention relates to oxidized normal paraffinic products. In particular this invention relates to said products and their application as flotation agents in, for example, minerals beneficiation, as well as in lubricants and drilling muds.

BACKGROUND OF THE INVENTION

Mixed fatty acids are obtainable from vegetable extraction or mammal is fat and lard. Natural fatty acids are of diverse sources and the composition and the saturation varies depending on the source of the material. The said natural organic compounds have various industrial applications such as flotation agents, in the production of detergents, as a wetting agent for insecticides, as synthetic lubricants in water-soluble applications and when esterified, as water soluble lubricants in drilling mud applications.

It is known in the art that natural organic carriers can be used in mineral flotation applications. One such natural fatty acid is oleic acid. This product is highly unsaturated and its composition varies.

It is known that unsaturation in the organic compound causes a large amount of gangue minerals to float together with the desired ore component. Therefore, a low purity rough concentrate will be obtained. This necessitates reflotation of the collected material using additional amounts of depressant. It can therefore be concluded, that the higher the degree of unsaturation the more tedious and costly the beneficiation process becomes.

It is also known that if the purity of the fatty acid is low and of varying composition, the recovery of the desired ore component will be lower and more unpredictable respectively, than expected, The ground ore will have to be refloated adding more collectors until the expected recovery is achieved.

The beneficiating process will again be less efficient the lower the purity and the more the composition of different batches of natural fatty acid varies.

Although the benefaction processes that are known in the art, and using the said natural products are effective, there nevertheless continues to exist the need for new processes and materials. In particular the disadvantage associated with the naturally obtained fatty acid products, i.e. the inconsistency of product composition and the purity that causes problems in formulating the dosages for the beneficiating process and the high degree of unsaturation present in the natural products that affects the flotation negatively (lower activity) that require higher dosage levels need to be addressed.

The inventors have now surprisingly found that by oxidizing a synthetically derived saturated hydrocarbon composition a final product of industrial grade can be obtained. Said product comprises a highly saturated fatty acid of known composition that also contains saturated alcohols. The product of the invention eliminates the disadvantages encountered in conventional applications with saturation and varying composition. The product of the present invention furthermore, has greater stability and longer life due to comparatively slower bio-degeneration.

SUMMARY OF THE INVENTION

According to a first aspect of the invention there is provided a flotation agent including an oxidised paraffinic product.

The paraffinic product may be a Fischer-Tropsch reaction product obtained by way of the Fischer-Tropsch reaction from CO (carbon monoxide) and $H_2$ (hydrogen) feed.

The paraffinic product may be Waksol™ obtainable from Schumann-Sasol.

According to a second aspect of the invention there is provided a process for the production of a synthetic fatty acid suitable as a substitute for naturally derived fatty acids In various applications.

In one embodiment of the invention the synthetic fatty acid may be applied in the beneficiation of minerals such as calcium fluoride, phosphate and coal.

The beneficiating process may comprise froth flotating a pulp conditioned with gangue metal depressant, where necessary and using the said synthetic fatty acid as a flotation and/or froth collecting agent.

The synthetic fatty acid may also be suitable for use as a synthetic lubricant in water-soluble lubricant applications. When esterified the synthetic fatty acid may be used as a water-soluble lubricant for drilling mud applications. When saponified with inorganic salts especially Calcium Hydroxide or esterified with various alcohols the product may be used as a corrosion protection agent.

According to a third aspect of the invention there is provided a minerals beneficiation process including the use of a synthetic fatty acid substantially as described above.

The minerals beneficiation process may be for the beneficiation of mineral ores containing phosphate, fluorspar and coal using oxidized Waksol as flotation agent.

The invention extends to the oxidation of Waksol, a commercial product of Schumann-Sasol (SA) Pty Ltd, having the physical and chemical properties as given in Example 1.

The oxidation of Fischer-Tropsch wax using standard oxidation processes and the properties and specification of the oxidized products which are suitable for the applications are given in Example 2.

The invention extends to the use of the oxidized Waksol as a synthetic water-soluble lubricant.

Without in any way limiting the invention, typical upper and lower limits of the process conditions useful for performing the invention as well as the values used are defined in the examples.

The present invention finds application in various fields, however, the list below is not exhaustive and is not intended to limit the scope of the invention. It will be dear to those skilled in the art that the Invention also has further applications.

- Oxide mineral beneficiation by means of flotation concentration
- Coal beneficiation by means of flotation concentration
- Production of synthetic water soluble lubricants
- Corrosion protection by forming a thin metal adhesive film Conventional applications of the applications listed above use mixed fatty acids obtained from the extraction of vegetation of mammal fat or lard. These materials are of low acid value and needs to be further oxidized to the desired acid number.

Some of the benefits of the synthetic fatty acid obtained from the invention are:

- Low relative degree of unsaturation when compared to the currently used fatty acids. The high degree of unsaturation render these natural fatty acids prone to flotation of gangue minerals which require higher dosages of gangue metal depressants than needed for the products of the invention. Higher purity resulting in a lower required dosage level. The lower purity of the fatty acids from natural origin render them less active resulting in higher required dosage for similar yields to the those of the products of the invention.

Lower biodegradation greater stability and longer shelf life when compared to the fatty acids from natural origin currently used in these technologies.

The water soluble lubricants from these products require less emulsion enhancing and stabilizing additives producing products with enhanced friction coefficients when compared to those currently used.

The corrosion protectors from these products have excellent adhesion to metal surfaces, good film forming ability and superion emulsifiality and lubricating properties.

The products of the invention can be applied in lubricants, as it also contains esters that are known to aid lubrication, in drilling fluids and as a froth collector in froth flotation applications and as corrosion protection agents.

Other specific advantages when applying the product of the present invention includes the high degree of saturation requiring lower dosage levels when compared to the known, high level unsaturated natural fatty acids.

In the water soluble lubricant applications, less emulsion stabilizing additives and emulsifiers are needed when using the product of the invention as compared to known technology.

In corrosion protection, providing both lubrication and rust prevention and because of the thin film ability, less product is applied when compared to conventional products.

The invention is now further illustrated by the following non-limiting examples. These examples emphasize the differences between the collectors produced by this invention and those collectors used in technologies known in the art especially oleic acid.

EXAMPLE 1

Physical and chemical properties of Waksol

The Fischer-Tropsch process produces a normal distribution range of hydrocarbons spanning $C_1$ to $C_{100}$. This range of hydrocarbons is separated by distillation. The Waksol Cut typically comprises a carbon number distribution ranging from approximately $C_{18}$ to $C_{38}$. Waksol suitable for the oxidation to produce oxy-Waksol typically has the following properties.

| PROPERTIES | TEST METHOD | UNITS | SPECIFICATION |
|---|---|---|---|
| Appearance | Sasol 1.34 | | Off-white to brown colour |
| Congealing point | ASTM D 938 | ° C. | 30 to 34 |
| Flash point at 101.3 kPa | ASTM D 93 | ° C. | 140 to 150 |
| Cloud point | Sasol 1.130 | ° C. | .40 to 60 |

EXAMPLE 2

Oxidation of Waksol 800 g of Waksol having the chemical and physical properties given in Example 1 was heated to 160C. for 80 minutes while blowing air at a rate of 2.31 per kilogram per second through the mixture. The temperature was decreased to 140° C. The oxidation was continued at this temperature and air flow until an acid value of 160 milligrams of potassium hydroxide per gram of oxidized material was obtained.

The chemical and physical properties of oxidized Waksol thus obtained are tabled below:

| Properties | Test method | Units | Specification |
|---|---|---|---|
| Acid Value | SS* no. 023/98 | Mg KOH/g | 160 min. |
| Appearance | Sasol 1.34 | visual | Brownviscous liquid |
| Flash point | ASTM D93 | ° C. | 70 min. |
| Specific Gravity | ASTM D 1298 | Kg/l | .90–.95 |
| Pour point | ASTM D 97 | ° C. | 10–15 |

*Schumann-Sasol test methods

EXAMPLE 3

In carrying out the process, the ore employed namely, phosphates, fluorspar and coal, is ground to a size suitable for froth flotation. Conventional grinding processes are used. This is typically such that a large portion could pass through a 80 micron screen.

After the conventional ground has been obtained, it is pulverized in water in accordance with the conventional froth procedures for flotation with fatty acids. The nature of the pulp should be the same as is customarily processed except for additives used in the processing.

After the grind is pulped, the pulp may be conditioned with suitable gangue depressants if necessary so as to obtain a satisfactory dispersion and effectively depress gangue minerals. The type and quantity of the depressant will vary and be significantly less than the typical values for oleic acid flotation. Nevertheless, the depressant is not a novel feature of this invention.

After the pulp is conditioned, it is subjected to froth flotation employing from 400 g to 600 g of fatty acid per ton of ore. Typically for fluorspar flotation, the dosage is 450 g per ton of ore if synthetic fatty acids from the invention is used instead of the 470 grams per ton when using natural fatty acids in the conventional process. This lower dosage is significant from an economic point of view and therefore makes the present invention highly lucrative.

The concentrate produced by the froth flotation is then collected by suitable procedures; normally those employed with conventional processes.

The basic principal behind mineral flotation is that the crude mineral ore is the treated with functionalised organic materials such as fatty acids, saturated alcohols or petroleum sulfonates, which render the desired mineral in the ground ore, hydrophobic. The desired mineral present In the froth floats on the water into a weir where it is collected.

Fluorspar flotation

The ore was ground to 80 % minus 100 micron. The ground ore was pulped in a flotation cell to a consistency suitable for flotation. The pulp was condition for 7 minutes with (collector and gangue depressants etc.) to obtain satisfactory pulp dispersion. Flotation was effected with staged additions with of oxy-Waksol. Each stage consists of 2 minutes of conditioning and 5 minutes of flotation.

Results given in the table below

| Fraction | Mass | % Mass | % $CaF_2$ | $CaF_2$ Mass | Recovery | % Fe | Fe Mass | Recovery | % $P_2O_5$ | $P_2O_5$ Mass | Recovery |
|---|---|---|---|---|---|---|---|---|---|---|---|
| Natural Fatty acids dosage = 472 gram/ton dry ore | | | | | | | | | | | |
| Heads | 1841.1 | 100.00 | 43.74 | 805.29 | | 54.14 | 996.71 | | 0.440 | 8.10 | |
| Conc. | 581.27 | 31.57 | 82.47 | 479.37 | 59.53 | 32.91 | 191.30 | 19.19 | 0.282 | 1.64 | 20.23 |
| Tails | 1259.83 | 68.43 | 25.87 | 325.92 | | 63.93 | 805.41 | | 0.513 | 6.46 | |
| Synthetic Fatty acids dosage = 451 gram/ton dry ore | | | | | | | | | | | |
| Heads | 1903.39 | 100.00 | 44.27 | 842.66 | | 52.75 | 1004.09 | | 0.430 | 8.10 | |
| Conc. | 685.83 | 36.03 | 88.32 | 605.73 | 71.88 | 32.91 | 225.71 | 22.48 | 0.282 | 1.93 | 23.64 |
| Tails | 1217.56 | 63.97 | 19.46 | 236.94 | | 63.93 | 778.39 | | 0.513 | 6.25 | |

Notes
The tests were conducted in a single bulk mass pull flotation procedure with cleaning stages to determine the reactivity and selectivity influence on the fluorspar ore.
Concentrate mass pull duration was 8 minutes

What is claimed is:

1. A flotation agent including an oxidized paraffinic product.

2. A flotation agent as claimed in claim 1, wherein the paraffinic product is a Fischer-Tropsch reaction product obtained by way of the Fischer-Tropsch reaction from CO (carbon monoxide) and $H_2$ (hydrogen) feed.

3. A flotation agent as claimed in claim 1, wherein the paraffinic product comprises a carbon number distribution ranging from approximately $C_{18}$ to $C_{36}$.

4. A process for the production of a synthetic fatty acid, which comprises heating a paraffinic product having a carbon number distribution ranging from about $C_{18}$ to $C_{36}$ in the presence of air for a sufficient time and at a sufficient temperature to obtain a synthetic fatty acid having an acid value of 160 mg of potassium hydroxide per gram of oxidized material.

5. A mineral beneficiation process, which comprises:

grinding an ore to obtain a ground ore having a size which will pass an 80 micron screen;

pulverizing the ground ore in order to obtain a pulp;

conditioning the pulp with an effective amount of gangue depressant to obtain a dispersion; and subjecting the dispersion to froth flotation using a synthetic acid having an acid value of 160 mg of potassium hydroxide per gram of oxidized material as a flotation agent.

6. The process according to claim 5, wherein the synthetic fatty acid has a specific gravity ranging from 0.9 to 0.95 Kg/l.

7. An oxidized paraffinic product having the following physical and chemical properties:

| PROPERTIES | TEST METHOD | UNITS | SPECIFICATION |
|---|---|---|---|
| Appearance | Sasol 1.34 | | Off-white to brown colour |
| Congealing point | ASTM D 938 | ° C. | 30 to 34 |
| Flash point at 101.3 kPa | ASTM D 93 | ° C. | 140 to 150 |
| Cloud point | Sasol 1.130 | ° C. | 40 to 60. |

* * * * *